United States Patent [19]
Poglitsch

[11] Patent Number: 5,746,093
[45] Date of Patent: May 5, 1998

[54] COMPENSATING DEVICE FOR COMPENSATION OF A TORQUE THAT DEPENDS ON THE ANGLE OF ROTATION, AND MEDICAL STAND WITH SUCH A COMPENSATING DEVICE

[75] Inventor: Christof Poglitsch, Aalen, Germany

[73] Assignee: Carl-Zeiss-Stiftung, Heidenheim, Germany

[21] Appl. No.: 603,969

[22] Filed: Feb. 22, 1996

[30] Foreign Application Priority Data

Mar. 11, 1995 [DE] Germany ............... 195 08 863.8

[51] Int. Cl.⁶ ............... F16M 11/12; G12B 3/00; G05D 17/02; G01L 3/00
[52] U.S. Cl. ............... 74/490.05; 188/166; 188/72.7; 248/280.11; 248/192.11
[58] Field of Search ............... 74/490.05, 490.01; 188/166, 83, 72.7, 72.8, 72.9; 248/585, 123.11, 280.11, 292.13, 292.11; 267/162

[56] References Cited

U.S. PATENT DOCUMENTS

| | | | |
|---|---|---|---|
| 3,396,931 | 8/1968 | Eckstein | 248/280.11 |
| 3,762,796 | 10/1973 | Heller | 350/85 |
| 3,762,797 | 10/1973 | Heller | 350/85 |
| 3,776,614 | 12/1973 | Kloots et al. | 350/35 |
| 3,891,301 | 6/1975 | Heller | 350/85 |
| 4,523,732 | 6/1985 | Biber et al. | 248/123.1 |
| 4,564,088 | 1/1986 | Takahashi | 188/166 |
| 5,263,694 | 11/1993 | Smith | 267/162 |
| 5,460,248 | 10/1995 | Korb | 188/166 |
| 5,553,821 | 9/1996 | Ishikawa | 248/292.11 |

*Primary Examiner*—Charles A. Marmor
*Assistant Examiner*—David M. Fenstermacher

[57] ABSTRACT

In a device for compensating a torque that depends on rotation angle and results from the rotational motion of a mass around a rotation axis, the rotational motion is converted into a linear displacement of a movably mounted displacement unit along a displacement axis in a defined manner depending on the rotation angle. The torque acting at any given time is compensated by an elastic compensating element that exerts a force opposite to the linear displacement of the displacement unit. Such a device is particularly suitable for compensation of torques that depend on rotation angle in medical stands.

5 Claims, 2 Drawing Sheets

COMPENSATING DEVICE FOR COMPENSATION OF A TORQUE THAT DEPENDS ON THE ANGLE OF ROTATION, AND MEDICAL STAND WITH SUCH A COMPENSATING DEVICE

BACKGROUND OF THE INVENTION

1. Field of the Invention

The present invention relates to a compensating device for compensation of a torque that depends on the angle of rotation, and which results during the rotational motion of a mass about an axis of rotation. The subject of the present invention is furthermore a medical stand with at least one axis of rotation with such a compensating device arranged on this axis of rotation.

2. Description of Prior Art

In medical technology, stands are known which serve for arranging and supporting many kinds of medical therapeutic and/or diagnostic instruments. Such stands usually include a series of axes of rotation so that, for example, operation microscopes can be positioned in space in a defined manner in several degrees of freedom, in order to assume as optimum as possible an observation position relative to the patient being operated on. The most extensive manipulations, with several degrees of freedom, are expected from the stands. Moreover, positioning that is free from effort and has a high degree of sensitivity is required for easy handling of the instruments arranged on the stand. In order to attain this objective, the torques produced by the respective masses about the various axes of rotation are as a rule compensated by counterweights or by spring kinematics.

Counterweight compensation mechanisms are known from U.S. Pat. Nos. 3,762,796; 3,762,797; and 3,891,301. A disadvantage associated with these counterweight compensation mechanisms is that in spite of the possible torque compensation, relatively high moments of inertia result during positioning about the axes being counterbalanced. A further disadvantage is the considerable increase in the weight of the whole system caused by the counterweights required. Moreover, an overall relatively bulky stand results from the use of such counterweight compensation mechanisms.

Spring mechanisms, which are known alternatives to these counterweight compensation mechanisms, in fact offer a passable compromise as regards weight and overall stand volume. However, it is not always possible to completely compensate the torques that arise. For example, such spring compensation mechanisms are described in U.S. Pat. Nos. 3,776,614 and 4,523,732.

The compensation of torques that depend on rotation angle is also problematic when using spring kinematics. In such cases, a variable compensating force that depends on rotation angle is required, and is not sufficiently ensured by the known arrangements. For example, this problem arises when, in the course of rotation of a mass, the weight of the mass makes a variable contribution to the torque occurring. In such a case, the axis of rotation is usually oriented at an angle other than 90° to the earth's surface.

These problems appear not only in medical stands, but also in other arrangements in which a torque depends on the rotation angle, and the torque that results from the rotation of a mass around an axis must be compensated at any given time.

SUMMARY OF THE INVENTION

The object of the present invention is to eliminate the disadvantages of the state of the art (as described above) and to provide a compactly constructed compensation device for the compensation of a torque that depends on the rotation angle. A further object of the invention is to provide a stand that includes such a compensating device.

This object is attained by a compensating device according to the invention, in which the rotational motion of the mass is converted into a defined linear motion of a movably mounted displacement unit. The displacement unit is mounted to be displaceable along a displacement axis. A compensating force exerted by a suitable elastic compensating element acts on the displacement unit according to its present linear displacement. The present linear displacement is dependent on the rotation angle. Thus, the torque which is acting at any given time can be compensated in a defined manner depending upon the respective rotation angle. For this purpose, the corresponding parameters of the compensating device are suitably dimensioned dependent upon the prescribed values, i.e., the dependence of the torque on the rotation angle.

The previously mentioned problem of heavy weight and overall stand volume required for torque compensation can now be avoided by means of the solution according to the invention. Furthermore, nearly a hundred percent compensation of the variable torque can be attained by a suitable choice of the elastic compensating element. In an advantageous embodiment of the compensating device according to the invention, this is possible by the dimensioning of cams that effect a defined preestablished linear displacement of the displacement unit in dependence on the rotation angle.

In principle, the apparatus according to the invention can be advantageously used on all axes which are to be counterbalanced. Moreover, it may be used in other fields.

BRIEF DESCRIPTION OF THE DRAWINGS

Further advantages, and also details of the invention, will become apparent from the following description of a preferred embodiment with reference to the accompanying drawings, in which.

DETAILED DESCRIPTION OF PREFERRED EMBODIMENTS

Figure 1:
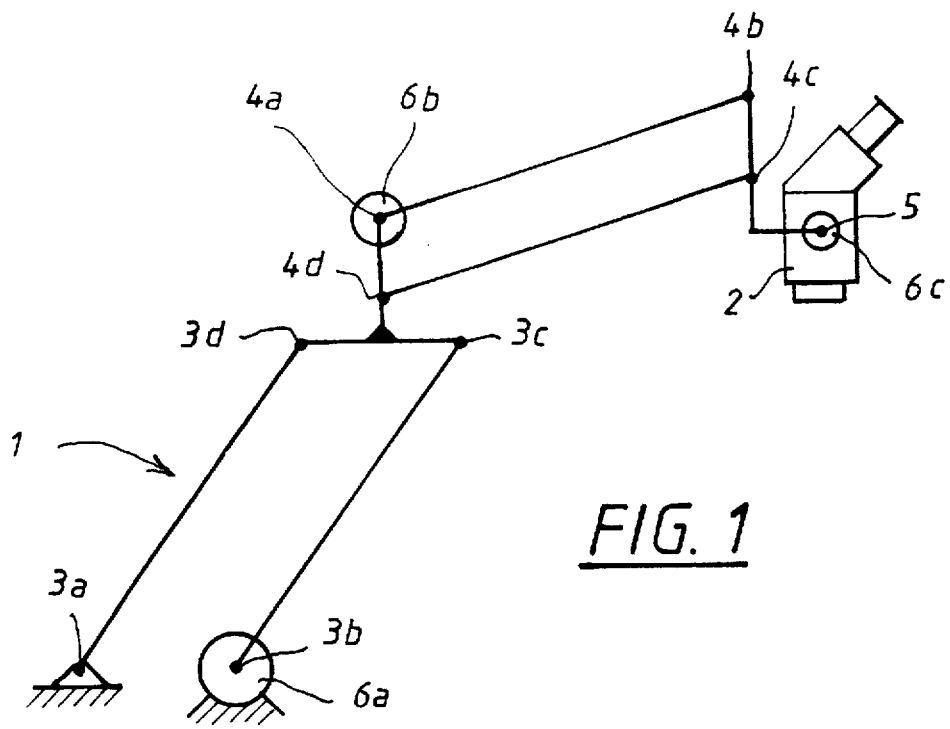
FIG. 1 shows a schematic illustration of a medical stand with several rotation axes, the compensating device according to the invention being integrated in some of the rotation axes.

FIG. 1 shows a schematic illustration of a medical stand (1) including an operation microscope (2) arranged thereon. The stand (1) has a substantially known double parallelogram structure, and is movable around a series of axes (3a, 3b, 3c, 3d, 4a, 4b, 4c, 4d), which in the illustration of FIG. 1 are all oriented perpendicular to the plane of the drawing. Furthermore, the operation microscope (2) is arranged to be rotatable around an axis (5) on the stand. This axis (5) has the same orientation as the rest of the stand axes (3a, 3b, 3c, 3d, 4a, 4b, 4c, 4d). Two of the rotation axes (3b, 4a) of the stand, and also the operation microscope rotation axis (5) have associated with them a respective compensating device (6a, 6b, 6c) according to the invention, by means of which compensation of the torques which act on them and which are dependent on the rotation angle is ensured. In the illustration of FIG. 1, the compensating devices (6a, 6b, 6c) associated with the rotation axes (3b, 4a, 5) are indicated only schematically. The preferred embodiment of the device according to the invention will be described with reference to FIGS. 2–4.

The orientation of the rotation axes (3b, 4a, 5) with the associated compensating devices (6a, 6b, 6c) does not change during the spatial positioning of the operation microscope (2) by means of the stand in the embodiment shown, i.e., the three axes (3b, 4a, 5) always remain aligned horizontally.

FIG. 1 shows one possible variant of the compensating device according to the invention. It is also possible to use the present invention in a stand that is otherwise constructed, or to counterbalance more or fewer axes of a stand with the present invention.

Figure 2:
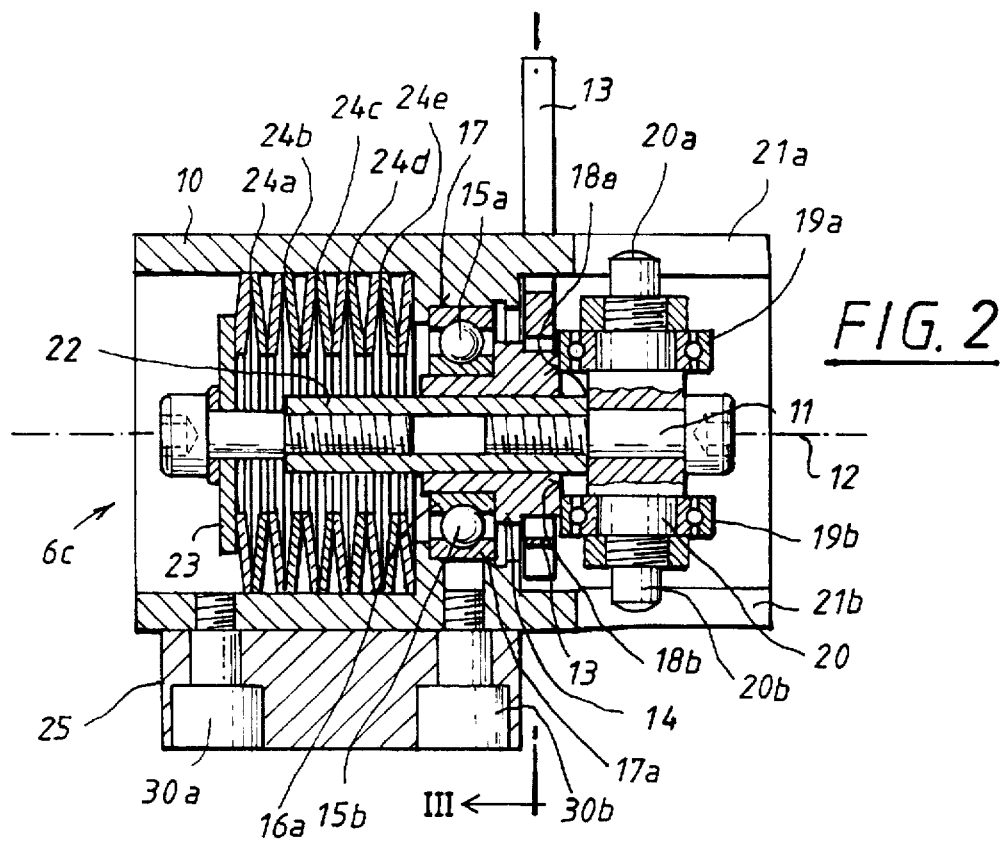
FIG. 2 shows a sectional view of a preferred embodiment of the compensating device according to the invention.

FIG. 2 shows a longitudinal section through an embodiment of the compensating device (6c) for the compensation of torques that are dependent on rotation angle.

Figure 3:
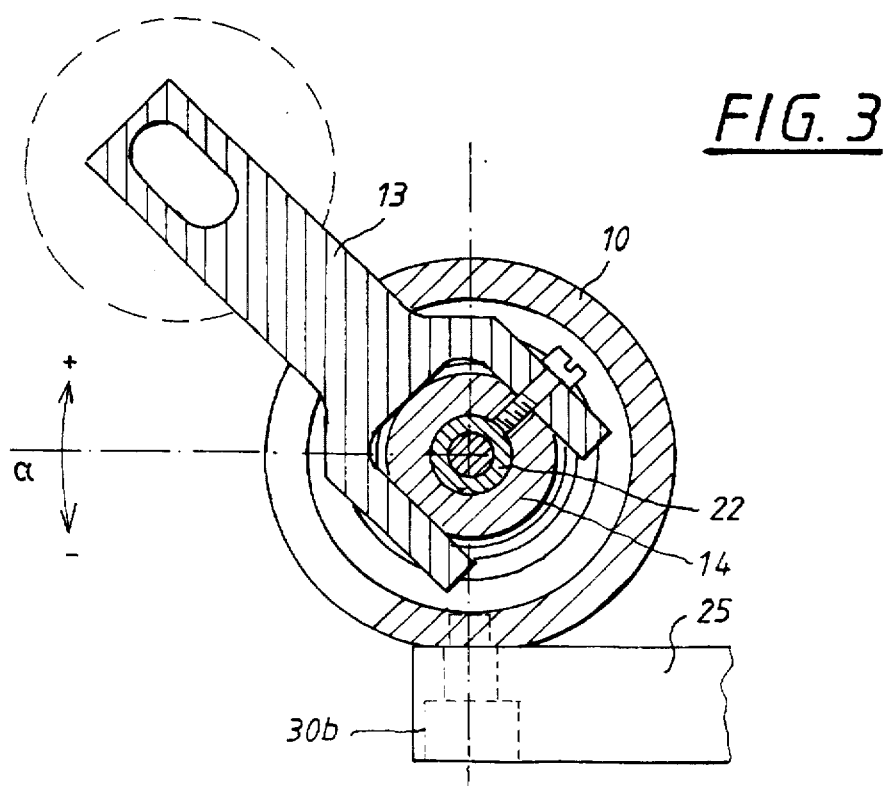
FIG. 3 shows a partial sectional view of the compensating device through section line III—III of FIG. 2.

FIG. 3 shows a sectional view through the plane labeled (III—III) in FIG. 2 of the compensating device (6c). The plane of the drawing coincides with the plane of rotation.

An embodiment of the compensating device (6c) is shown in FIGS. 2 and 3 in a form suitable for arrangement on the operation microscope rotation axis having the reference symbol (5) in FIG. 1. A part (25) of the stand to which the compensating device (6c) is attached by screw connections (30a, 30b) can be seen in both FIGS. 2 and 3.

A displacement unit (11), which is linearly displaceable along a displacement axis (12), is mounted in a cylindrical housing (10) of the compensating device (6c). The displacement axis (12) coincides with the longitudinal axis of the cylindrical housing (10) and the rotation axis (5). The rotational motion of the respective mass takes place around the displacement axis (12). The torques arising from this rotary motion and dependent on the rotation angle must be compensated by the compensating device (6c) according to the invention.

The precise linear guiding of the displacement unit (11) along the displacement axis (12) is ensured by means of two guide grooves (21a, 21b) in the housing (10) of the compensating device into which two guide pins (20a, 20b) of the displacement unit (11) engage.

The mass to be rotated, or the operation microscope in this case, is not shown in FIG. 2 for reasons of clarity. Only a connecting element (13) can be seen, on which the operation microscope is arranged and connected to the compensating device (6c). The connecting element (13) passes out of the housing (10) of the compensating device (6c) through an aperture.

The connecting element (13) is connected to a sleeve (14) which is arranged to be rotatable about the displacement axis (12) (or the rotation axis (5)). The sleeve (14) is stationary in the longitudinal direction of the displacement axis (12). A ball bearing (15a, 15b, 16a, 17a), arranged with radial symmetry around the displacement axis (12), is provided for mounting the sleeve (14) for rotation around the displacement axis (12), and facilitates as frictionless as possible a rotation of the sleeve (14). The ball bearing (15a, 15b, 16a, 17a) includes a ball bearing inner ring (16a) that adjoins a flange-shaped bearing surface of the rotatable sleeve (14). The ball bearing also includes a ball bearing outer ring (17a) that adjoins a stationary mounting surface (17) of the housing (10), and the individual balls (15a, 15b) that lie between the rings.

At the longitudinal end opposite to the flange-shaped mounting surface (16), the sleeve (14) has two symmetrical cams (18a, 18b). The reference symbols (18a) and (18b) in FIG. 2 denote the surfaces of the cams against which the displacement unit (11) is supported by means of two ball-mounted, rotatable rings (19a, 19b). The ball-mounted, rotatable rings are arranged on a support section (20) of the displacement unit (11). The rotation axis of these rotatable rings (19a, 19b) is oriented respectively perpendicular to the displacement axis (12).

Figure 4C:
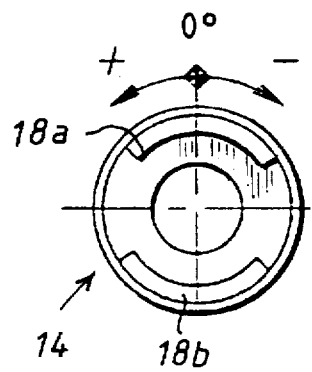
FIGS. 4a–4c show respectively perspective, sectional and plan views of an element of the embodiment according to FIGS. 2 and 3.
Figure 4B:
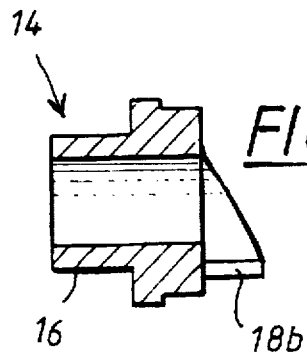
Figure 4A:
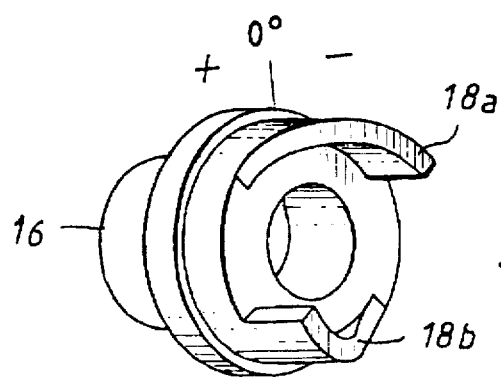

The arrangement of the two symmetrical cams or of the corresponding bearing faces (18a, 18b) on which the displacement unit is supported, and also the construction of the sleeve (14), are apparent from the various partial views of the sleeve (14) in FIGS. 4a–4c.

Preferably, at least the bearing faces (18a, 18b) of the cams are hardened, in order to ensure a certain useful life of the device according to the invention even in the case where it is acted on by high torques or linear forces.

Besides the support section (20) with the previously described guide pins (20a, 20b), the displacement unit (11) includes a cylindrical traction rod (22) that is mounted within the sleeve (14) to be movable in the displacement direction, i.e., in the longitudinal direction of the housing. The support section (20), which is supported on the cams (18a, 18b) by means of the ball-mounted rings (19a, 19b) can be screwed and fastened to one end of the traction rod (22). A plate (23) is arranged via a screw connection at the other end of the traction rod (22), and on it are supported a series of adjacently arranged plate springs (24a, 24b, 24c, 24d, 24e). The plate springs (24a, . . . , 24e) are supported on a fixed projection of the housing (10) of the compensating device (6c), and exert a compensating force that opposes the torque acting on the displacement unit (11), when the displacement unit (11) is displaced to the right in FIG. 2.

Thus, if rotation of the connecting element (13) or of the mass perpendicularly to the plane of the drawing around the rotation axis takes place, the displacement unit (11) is displaced to the right in the longitudinal direction on the rotation axis, by the selected slope of the cams. However, the spring force of the then compressed plate springs (24a, . . . 24e) simultaneously acts against the displacement to the right. A defined preestablished compensation of the torque acting at any given time can be attained by the corresponding dimensioning of the plate springs (24a, . . . ,24e). For this purpose, the plate springs (24a, . . . ,24e) must be combined such that according to the degree of compensation a corresponding counter-force to the acting torque results. Moreover the slope of the cams is to be chosen such that a defined predetermined linear displacement of the displacement unit (11) along the displacement axis, or rotation axis (12), always takes place in dependence on the rotation angle (a in FIG. 3). According to the resulting displacement, the correspondingly dimensioned compensating force of the plate springs (24a, . . . , 24e) then acts, and compensates for the acting torque.

FIG. 3 shows a sectional illustration of the compensating device according to the invention, in the plane of rotation. The connecting element (13) on which the mass to be rotated is arranged, is now clearly apparent. The same reference symbols are used as in FIG. 2 for the same parts.

Besides the possible use of plate springs as in the previously described embodiment, it is also possible to insert other elastic compensating elements, which compensate for the respective torque, within the compensating device according to the invention. For example, other springs, hydraulics, gas pressure, compressed air and similar systems may be used. The required elastic compensating elements are selected or dimensioned dependending upon the torques to be compensated for.

The dimensioning of the cams and also the corresponding dimensioning of the elastic compensating elements takes place in an iterative calculation process. The parameters to be fitted are optimized stepwise depending upon the rotation angle and the other conditions that are given in advance.

Besides the embodiment described, further possibilities of mechanical and constructional embodiments of the compensating device according to the invention exist. In the concept according to the invention, what is important at any given time is the conversion of the rotary motion of the respective mass into a linear motion of the displacement unit, which acts against a compensating force of elastic compensating elements.

The respective linear displacement is selected in a defined relationship to the dependence of the acting torque on the rotation angle. The respective dependence of the torque on the rotation angle remains the same for only a given spatial orientation of the rotation axis, i.e., in the case of another orientation of the rotation axis, another dependence results. However, it is also possible to determine a correspondingly shaped cam for a relationship of a different kind between the rotation angle and the resulting torque, i.e., even for other orientations than the described horizontal orientation of the rotation axis. The device according to the invention can thus be flexibly matched to varied situations.

I claim:

1. A compensating device for compensating a torque that depends on rotation angle and results from rotational motion of a mass around a rotation axis (3b, 4a, 5) comprising:

a movably mounted displacement unit (11) arranged for linear displacement along a displacement axis, which linear displacement is caused by said rotational motion and depends on said rotation angle, at least one elastic compensating element (24a, 24b, 24c, 24d, 24e) that is arranged to exert on said displacement unit (11) a compensating force in a direction opposite to said linear displacement of said displacement unit (11), which compensating force depends on said linear displacement of said displacement unit, wherein said compensating device compensates for torque acting at any given time, at least one connecting element (13) for connecting said mass to said compensating device, and a sleeve (14) with at least one cam (18a, 18b), mounted rotatably around said displacement axis (12) and connected to said connecting element (13), wherein said displacement unit (11) is arranged to be urged into contact with said at least one cam (18a, 18b) of said sleeve (14), and said displacement unit (11) is provided with at least one ball bearing (19a, 19b) that is arranged to roll on said cam (18a, 18b) during rotational motion of said mass.

2. The compensating device according to claim 1, wherein said displacement unit (11) includes a traction rod (22) and a support section (20) arranged at one end of said traction rod (22) for supporting said displacement unit (11) by said at least one cam (18a, 18b) against a compensating force of said elastic compensating element (24a, 24b, 24c, 24d 24e).

3. The compensating device according to claim 2, wherein said sleeve (14) is provided with two symmetrical cams (18a, 18b), and said support section (20) is provided with two ball bearings (19a, 19b) that are arranged to roll respectively on said two symmetrical cams (18a, 18b) during rotational motion of said support section (20).

4. The compensating device according to claim 2, wherein said traction rod (22) has a plate-shaped construction at its other end, and said at least one elastic compensating element (24a, . . . 24e) is supported against a surface of said plate-shaped construction.

5. The compensating device according to claim 4, wherein said at least one elastic compensating element (24a, . . . 24e) comprises a plurality of plate springs arranged one behind another.

\* \* \* \* \*